United States Patent
Blasco et al.

(10) Patent No.: US 7,148,227 B2
(45) Date of Patent: *Dec. 12, 2006

(54) FUNGICIDAL TRIAZOLOPYRIMIDINES, METHODS FOR PRODUCING THE SAME, USE THEREOF FOR COMBATING HARMFUL FUNGI AND AGENTS CONTAINING SAID SUBSTANCES

(75) Inventors: Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Hessheim (DE); Anja Schwögler, Mannheim (DE); Eberhard Ammermann, Heppenheim (DE); Siegfried Strathmann, Limburgerhof (DE); Gisela Lorenz, Neustadt (DE); Reinhard Stierl, Freinsheim (DE); Ulrich Schöfl, Brühl (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/508,409

(22) PCT Filed: Mar. 19, 2003

(86) PCT No.: PCT/EP03/02847

§ 371 (c)(1),
(2), (4) Date: Sep. 21, 2004

(87) PCT Pub. No.: WO03/080615

PCT Pub. Date: Oct. 2, 2003

(65) Prior Publication Data

US 2005/0176736 A1    Aug. 11, 2005

(30) Foreign Application Priority Data

Mar. 21, 2002 (DE) .................. 102 12 739
Apr. 10, 2002 (DE) .................. 102 15 814
Dec. 11, 2002 (DE) .................. 102 58 050

(51) Int. Cl.
*A61K 31/519* (2006.01)
*C07D 487/04* (2006.01)
*C07C 69/738* (2006.01)

(52) U.S. Cl. .................. 514/259.31; 544/263; 560/51

(58) Field of Classification Search .......... 514/259.31; 544/263; 560/51

See application file for complete search history.

(56) References Cited

U.S. PATENT DOCUMENTS

| | | | | |
|---|---|---|---|---|
| 4,567,263 A | | 1/1986 | Eicken et al. | 544/263 |
| 5,270,313 A | | 12/1993 | Burri et al. | 514/252.02 |
| 5,656,573 A | * | 8/1997 | Roberts et al. | 504/271 |
| 5,985,883 A | | 11/1999 | Pees | 514/259.31 |
| 6,114,532 A | | 9/2000 | Ries et al. | 546/162 |
| 6,284,762 B1 | * | 9/2001 | Pfrengle | 514/259.31 |

FOREIGN PATENT DOCUMENTS

| | | |
|---|---|---|
| EP | 394 644 | 10/1990 |
| EP | 410 244 | 1/1991 |
| EP | 418 175 | 3/1991 |

(Continued)

OTHER PUBLICATIONS

Beare et al., Journal of Organic Chemistry (2002) 67(2), 541-555 (XP002245228).

(Continued)

*Primary Examiner*—Mark Berch
*Assistant Examiner*—Susanna Moore
(74) *Attorney, Agent, or Firm*—Novak Druce & Quigg, LLP

(57) ABSTRACT

The invention relates to triazolopyrimidines of formula (I), in which the substituents are defined as follows: $L^1$ represents cyano, $S(=O)_n A^1$ or $C(=O)A^2$, wherein $A^1$ stands for hydrogen, hydroxy, alkyl, alkylamino or dialkylamino; $A^2$ stands for $C_1$–$C_8$ alkoxy, $C_1$–$C_6$ haloalkoxy or one of the groups named in $A^1$; and n stands for 0, 1 or 2; $L^2$, $L^3$ represent hydrogen or halogen; $L^4$, $L^5$ represent hydrogen, halogen or alkyl; X represents halogen, cyano, alkyl, haloalkyl, alkoxy or haloalkoxy; $R^1$ represents alkyl, haloalkyl, cycloalkyl, halocycloalkyl, alkenyl, alkadienyl, haloalkenyl, cycloalkenyl, alkynyl, haloalkynyl or cycloalkynyl, phenyl, naphthyl, or a five to ten-membered saturated, partially unsaturated or aromatic heterocyclus containing between one and four heteroatoms from the group containing O, N or S; $R^2$ represents hydrogen or $R^1$; $R^1$ and $R^2$ can form, together with the nitrogen atom to which they are bonded, a five or six-membered ring, which can be interrupted and/or substituted by an atom from the group O, N and S; whereby $R^1$ and/or $R^2$ can be substituted in accordance with the description. The invention also relates to methods and intermediate products for producing said compounds, to agents containing the latter and to the use of said compounds for combating harmful fungi.

10 Claims, No Drawings

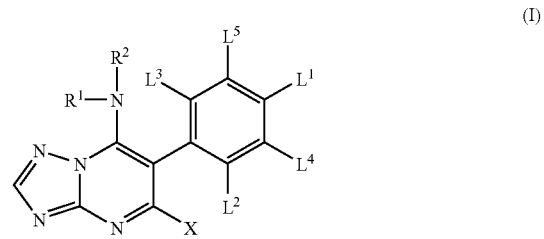

FOREIGN PATENT DOCUMENTS

| | | |
|---|---|---|
| EP | 550 113 | 7/1993 |
| EP | 770 615 | 5/1997 |
| EP | 834 513 | 4/1998 |
| EP | 945 453 | 9/1999 |
| GB | 2 217 710 | 11/1989 |
| WO | 98/46607 | 10/1998 |
| WO | 98/46608 | 10/1998 |
| WO | WO 98/46608 A1 * | 10/1998 |
| WO | 99/41255 | 8/1999 |
| WO | 99/48893 | 9/1999 |
| WO | 02/02563 | 1/2002 |
| WO | 02/46195 | 6/2002 |
| WO | 02/50077 | 6/2002 |
| WO | 03/008417 | 1/2003 |

OTHER PUBLICATIONS

Chemical Abstract Service, Columbus, Ohio; Ikeno, Ikuyo (XP 002245232).

Tona, Merce et al; Tetrahedron (1995), 51(36), 10041-52 8 (XP 002245229) Tona, Merce et al; Tetrahedron (1995), 51(36), 10041-52 8 (XP 002245229).

Tona, Merce et al.; Tetrahedron (1994), 50(27), 8227-26 (XP 002245230).

Chemical Abstract Service, Columbus, Ohio; Dell'Erba, Carlo et al. (XP 002245233).

Chemical Abstract Service; Columbus, Ohio; Narita, Hirokazu et al; (XP 002245234).

Momose, Tsutomu et al; Chemical & Pharmaceutical Bulletin (1958), 6, 415-21.

Chemical Abstract Service; Columbus, Ohio; Vlasov., V.M. et al; (1977), (5), 127-36 (XP002245235).

Hennessy et al.; Organic Letters, Bd. 4 No. 2, 2002, pp. 269-272; (XP 002245231).

Guenther Fischer; Advances in Heterocyclic Chemistry, vol. 57.

* cited by examiner

FUNGICIDAL TRIAZOLOPYRIMIDINES, METHODS FOR PRODUCING THE SAME, USE THEREOF FOR COMBATING HARMFUL FUNGI AND AGENTS CONTAINING SAID SUBSTANCES

The present invention relates to triazolopyrimidines of the formula I,

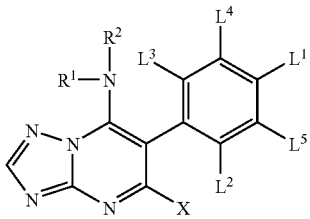

I in which substituents have the following meanings:
- $L^1$ is cyano, $S(=O)_n A^1$ or $C(=O)A^2$, wherein
  - $A^1$ is hydrogen, hydroxyl, $C_1$–$C_8$-alkyl, $C_1$–$C_8$-alkylamino or di($C_1$–$C_8$-alkyl)amino;
  - $A^2$ is $C_1$–$C_8$-alkoxy, $C_1$–$C_6$-haloalkoxy or one of the groups mentioned under $A^1$;
  - n is 0, 1 or 2;
- $L^2$,$L^3$ are hydrogen or halogen;
- $L^4$,$L^5$ are hydrogen, halogen or $C_1$–$C_4$-alkyl;
- X is halogen, cyano, $C_1$–$C_4$-alkyl, $C_1$–$C_4$-haloalkyl, $C_1$–$C_4$-alkoxy or $C_1$–$C_2$-haloalkoxy;
- $R^1$ is $C_1$–$C_8$-alkyl, $C_1$–$C_8$-haloalkyl, $C_3$–$C_6$-cycloalkyl, $C_3$–$C_6$-halocycloalkyl, $C_2$–$C_8$-alkenyl, $C_4$–$C_{10}$-alkadienyl, $C_2$–$C_8$-haloalkenyl, $C_3$–$C_6$-cycloalkenyl, $C_2$–$C_8$-alkynyl, $C_2$–$C_8$-haloalkynyl or $C_3$–$C_6$-cycloalkynyl, phenyl, naphthyl, or a five- to ten-membered saturated, partially unsaturated or aromatic heterocycle, comprising one to four heteroatoms from the group consisting of O, N and S;
- $R^2$ is hydrogen or one of the groups mentioned under $R^1$,
- $R^1$ and $R^2$ can also, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain;
- wherein $R^1$ and/or $R^2$ can be substituted by one to four identical or different groups $R^a$:
- $R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di($C_1$–$C_6$-alkyl)amino, $C_2$–$C_6$-alkenyl, $C_2$–$C_6$-alkenyloxy, $C_3$–$C_6$-alkynyloxy, $C_3$–$C_6$-cycloalkyl, phenyl, naphthyl or a five- to ten-membered saturated, partially unsaturated or aromatic heterocycle, comprising one to four heteroatoms from the group consisting of O, N and S,
  - wherein these aliphatic, alicyclic or aromatic groups, for their part, can be partially or completely halogenated or can carry one to three groups $R^b$:
- $R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl or dialkylaminothiocarbonyl, wherein the alkyl groups in these radicals comprise 1 to 6 carbon atoms and the alkenyl or alkynyl groups mentioned in these radicals comprise 2 to 8 carbon atoms;
  - and/or one to three of the following radicals:
  - cycloalkyl, cycloalkoxy, heterocyclyl or heterocyclyloxy, wherein the cyclic systems comprise 3 to 10 ring members; aryl, aryloxy, arylthio, aryl-$C_1$–$C_6$-alkoxy, aryl-$C_1$–$C_6$-alkyl, hetaryl, hetaryloxy or hetarylthio, wherein the aryl radicals preferably comprise 6 to 10 ring members and the hetaryl radicals comprise 5 or 6 ring members, wherein the cyclic systems can be partially or completely halogenated or can be substituted by alkyl or haloalkyl groups.

The invention relates in addition to processes for and intermediates in the preparation of these compounds, compositions comprising them and their use in the control of harmful fungi.

5-Chlorotriazolopyrimidines for the control of harmful fungi are known from EP-A 71 792, EP-A 550 113, WO-A 98/46608 and WO-A 99/41255.

Fungicidally effective triazolopyrimidines having specific substitution of the 6-phenyl group are known from EP-A 834 513, WO 98/46607, EP-A 945 453, WO 99/48893, U.S. Pat. No. 5,985,883 and WO 02/46195.

However, in many cases, in particular when low amounts are applied, their action is not always satisfactory.

It is the object of the present invention to provide compounds with an improved action and/or a broadened spectrum of activity.

We have found that this object is achieved with the compounds defined at the start. Processes for and intermediates in their preparation, compositions comprising them and processes for the control of harmful fungi through the use of the compounds I have also been found.

The compounds of the formula I are distinguished from those from the abovementioned documents in the substitution of the 6-phenyl group, which carries a group $L^1$ in the para-position, and the substitution of the 7-amino group.

The compounds of the formula I have, in comparison with the known compounds, an increased activity against harmful fungi. The compounds according to the invention can be obtained in various ways. They are advantageously prepared by reaction of 5-aminotriazole of the formula II with appropriately substituted phenylmalonates of the formula III in which R is alkyl, preferably $C_1$–$C_6$-alkyl, in particular methyl or ethyl.

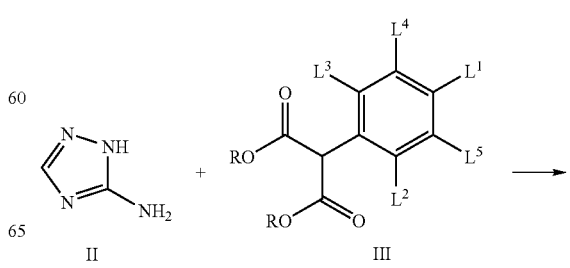

-continued

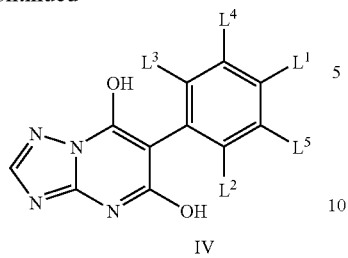

IV

This reaction is usually carried out at temperatures of 80° C. to 250° C., preferably 120° C. to 180° C., without solvent or in an inert organic solvent, in the presence of a base [cf. EP-A 770 615] or in the presence of acetic acid under the conditions known from Adv. Het. Chem., Vol. 57, pp. 81ff. (1993).

Suitable solvents are aliphatic hydrocarbons, aromatic hydrocarbons, such as toluene or o-, m- and p-xylene, halogenated hydrocarbons, ethers, nitriles, ketones, alcohols, N-methylpyrrolidone, dimethyl sulfoxide, dimethylformamide and dimethylacetamide. In a particularly preferred way, the reaction is carried out without solvent or in chlorobenzene, xylene, dimethyl sulfoxide, N-methylpyrrolidone. Mixtures of the solvents mentioned can also be used.

Suitable bases are generally inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, alkali metal hydrogencarbonates, or organometallic compounds, in particular alkali metal alkyls, alkyl magnesium halides, and alkali metal and alkaline earth metal alkoxides and magnesium dimethoxide, as well as organic bases, e.g. tertiary amines, such as trimethylamine, triethylamine, triisopropylethylamine, tributylamine, N-methylpiperidine and N-methylmorpholine, pyridine, substituted pyridines, such as collidine, lutidine and 4-dimethylaminopyridine, and bicyclic amines. Tertiary amines, such as triisopropylethylamine, tributylamine, N-methylmorpholine or N-methylpiperidine, are especially preferred.

The bases are generally used in catalytic amounts. However, they can also be used in equimolar amounts, in excess or possibly as solvent.

The starting materials are generally reacted with one another in equimolar amounts. It can be advantageous to the yield to use the base and the malonate III in an excess with respect to the triazole.

Phenylmalonates of the formula III are advantageously obtained from the reaction of suitably substituted bromobenzenes with dialkyl malonates under Cu(I) catalysis [cf. Chemistry Letters, pp. 367–370, 1981; EP-A 10 02 788].

The dihydroxytriazolopyrimidines of the formula IV are converted to the dihalopyrimidines of the formula V under the conditions known from WO-A 94/20501. A chlorinating agent or a brominating agent, such as phosphorus oxybromide or phosphorus oxychloride, optionally in the presence of a solvent, is advantageously used as halogenating agent [Hal].

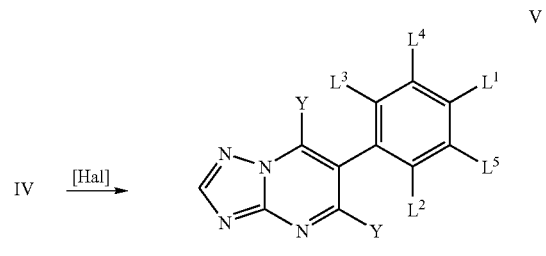

This reaction is usually carried out at 0° C. to 150° C., preferably at 80° C. to 125° C. [cf. EP-A 770 615].

Dihalopyrimidines of the formula V are further reacted with amines of the formula VI,

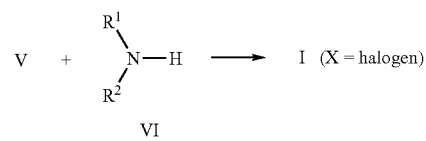

in which $R^1$ and $R^2$ are defined as in formula I, to give compounds of the formula I in which X is halogen.

This reaction is advantageously carried out at 0° C. to 70° C., preferably 10° C. to 35° C., preferably in the presence of an inert solvent, such as ethers, e.g. dioxane, diethyl ether or, particularly, tetrahydrofuran, halogenated hydrocarbons, such as dichloromethane, and aromatic hydrocarbons, such as, for example, toluene [cf. WO-A 98/46608].

The use of a base, such as tertiary amines, for example triethylamine, or inorganic amines, such as potassium carbonate, is preferred; in addition, excess amine of the formula VI can be used as a base.

Compounds of the formula I in which X represents cyano, $C_1$–$C_6$-alkoxy or $C_1$–$C_2$-haloalkoxy can advantageously be obtained from the reaction of compounds I, in which X represents halogen, preferably chlorine, with compounds M-X' (formula VII). Compounds VII represent, depending on the meaning of the group X' to be introduced, an inorganic cyanide, an alkoxide or a haloalkoxide. The reaction is advantageously carried out in the presence of an inert solvent. The cation M in formula VII is of little importance; for practical reasons, ammonium, tetraalkylammonium, alkali metal or alkaline earth metal salts are usually preferred.

$$I(X\text{=halogen}) + M\text{-}X' \rightarrow I(X\text{=}X') \qquad \text{VII}$$

The reaction temperature usually lies between 0 and 120° C., preferably between 10 and 40° C. [cf. J. Heterocycl. Chem., Vol. 12, pp. 861–863 (1975)].

Suitable solvents include ethers, such as dioxane, diethyl ether and, preferably, tetrahydrofuran, halogenated hydrocarbons, such as dichloromethane, and aromatic hydrocarbons, such as toluene.

Compounds of the formula I in which X is $C_1$–$C_4$-alkyl or $C_1$–$C_4$-haloalkyl can advantageously be obtained through the following synthetic route:

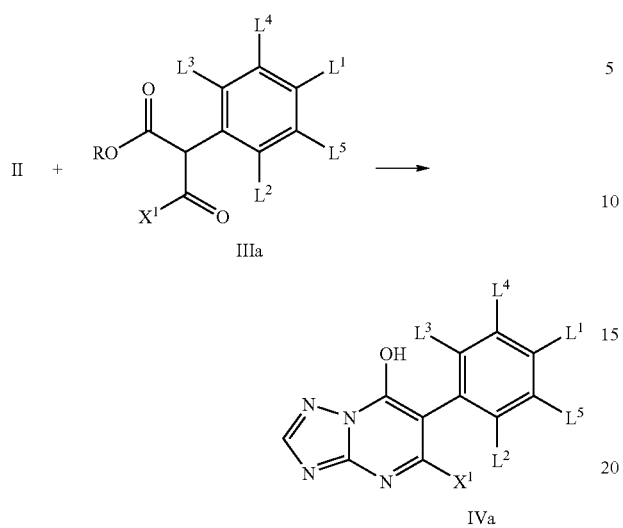

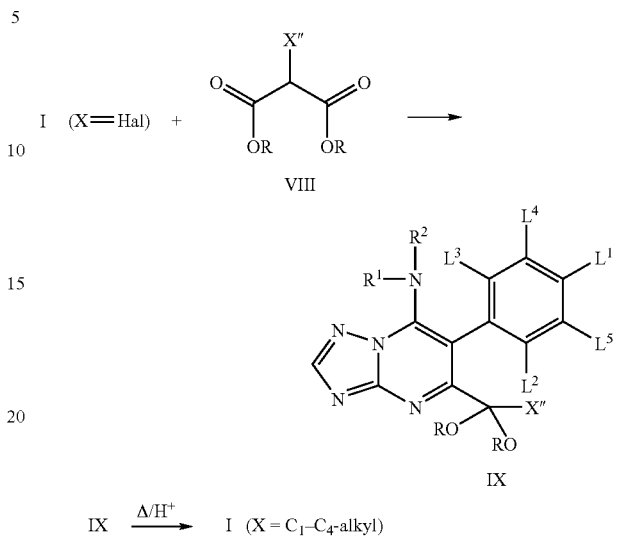

The 5-alkyl-7-hydroxy-6-phenyltriazolopyrimidines IVa are obtained from the ketoesters IIIa. The 5-methyl-7-hydroxy-6-phenyltriazolopyrimidines are obtained through the use of the readily accessible 2-phenylacetoacetic esters (IIIa with $X^1$=$CH_3$) [cf. Chem. Pharm. Bull., 9, 801, (1961)]. The preparation of the starting compounds IIIa is advantageously carried out under the conditions described in EP-A 10 02 788.

The 5-alkyl-7-hydroxy-6-phenyltriazolopyrimidines obtained in this way are reacted with halogenating agents [Hal] to give the 7-halotriazolopyrimidines of the formula Va. Chlorinating or brominating agents, such as phosphorus oxybromide, phosphorus oxychloride, thionyl chloride, thionyl bromide or sulfuryl chloride, are preferably used. The reaction can be carried out in bulk or in the presence of a solvent. Usual reaction temperatures are from 0 to 150° C. or, preferably, from 80 to 125° C.

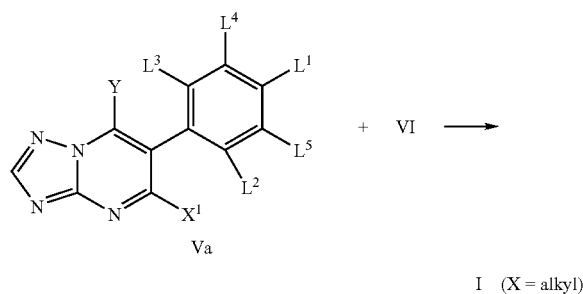

The reaction of Va with amines VI is carried out under the conditions described further above.

Compounds of the formula I in which X represents $C_1$–$C_4$-alkyl can alternatively also be prepared from compounds I in which X represents halogen, in particular chlorine, and malonates of the formula VIII. In formula VIII, X" represents hydrogen or $C_1$–$C_3$-alkyl and R represents $C_1$–$C_4$-alkyl. They are reacted to give compounds of the formula IX and are decarboxylated to give compounds I [cf. U.S. Pat. No. 5,994,360].

$$IX \xrightarrow{\Delta/H^+} I \quad (X = C_1\text{–}C_4\text{-alkyl})$$

The malonates VIII are known in the literature [J. Am. Chem. Soc., Vol. 64, 2714 (1942); J. Org. Chem., Vol. 39, 2172 (1974); Helv. Chim. Acta, Vol. 61, 1565 (1978)] or can be prepared according to the literature cited.

The subsequent saponification of the ester IX is carried out under generally standard conditions. Depending on the various structural components, the alkaline or the acidic saponification of the compounds IX may be advantageous. Under the conditions of the saponification of esters, the decarboxylation to give I may already take place, completely or partially.

The decarboxylation usually takes place at temperatures of 20° C. to 180° C., preferably 50° C. to 120° C., in an inert solvent, optionally in the presence of an acid.

Suitable acids are hydrochloric acid, sulfuric acid, phosphoric acid, formic acid, acetic acid and p-toluenesulfonic acid. Suitable solvents are water, aliphatic hydrocarbons, such as pentane, hexane, cyclohexane and petroleum ether, aromatic hydrocarbons, such as toluene and o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, dimethyl sulfoxide, dimethylformamide and dimethylacetamide. In a particularly preferred way, the reaction is carried out in hydrochloric acid or acetic acid. Mixtures of the solvents mentioned can also be used.

Compounds of the formula I in which X is $C_1$–$C_4$-alkyl can also be obtained by coupling of 5-halotriazolopyrimidines of the formula I in which X represents halogen with organometallic reagents of the formula X. In an embodiment of this process, the reaction is carried out under transition metal catalysis, such as Ni or Pd catalysis.

$$I(X\text{=halogen}) + M^Y(\!-\!R^2)_Y \rightarrow I \qquad X$$

In formula X, M is a metal ion with a valency of Y, such as, for example, B, Zn or Sn. This reaction can be carried out, for example, analogously to the following methods: J. Chem. Soc. Perkin Trans., 1, 1187 (1994), ibid, 1, 2345 (1996); WO-A 99/41255; Aust. J. Chem., Vol. 43, 733 (1990); J. Org. Chem., Vol. 43, 358 (1978); J. Chem. Soc. Chem. Commun., 866 (1979); Tetrahedron Lett., Vol. 34, 8267 (1993); ibid, Vol. 33, 413 (1992).

If $R^1$ and $R^2$ represent halogen-free groups, optically active amines of the formula VI in the (R)-configuration are preferred.

If $R^1$ or $R^2$ comprises haloalkyl or haloalkenyl groups, the (S)-configuration is preferred for optically active amines of the formula VI.

Amines of the formula VI are either commercially available or, if they have a center of chirality, are accessible through resolution according to WO 02/38565. For example, (R)-3,3-dimethylbut-2-amine (R-DMBA) can particularly advantageously be prepared in this way.

In a preferred embodiment of the process according to the invention for the preparation of the compounds in which $L^1$ represents $S(=O)_nA^1$ with n=1 or 2, the thio compounds with n=0 are oxidized at the formula I stage [Lit.: WO 94/14761; Synth, Commun., Vol. 16, p. 233 (1986)].

Compounds of the formulae I, III and IV in which $L^1$ is $S(=O)_nA^1$ with n=2 and $A^1$ is alkyl, in particular methyl, can also be used as intermediates in the preparation of additional 6-phenyltriazolopyrimidines. These intermediates can advantageously be used for the preparation of those triazolopyrimidines in which the 6-phenyl group exhibits in the para-position a group which can be introduced as a nucleophile, such as, for example, cyano, nitro, hydroxyl, alkoxy, haloalkoxy or groups bonded via nitrogen, such as alkylamino, dialkylamino or a heterocycle bonded via N [Lit.: Tetrahedron Lett., p. 759 (1967); ibid p. 1763 (2000); J. Org. Chem., p. 4705 (1979)]. The exchange of the $SO_2$ alkyl group with the substituent to be introduced takes place particularly advantageously at the formula I stage.

Compounds of the formula I in which $L^1$ is $C(=O)A^2$ with $A^2$=hydrogen or alkyl are advantageously prepared from the corresponding compounds in which $L^1$ is CN. This conversion is carried out particularly preferably at the formula I stage.

Compounds in which $L^1$ represents CHO are preferably prepared from the corresponding cyanides by reduction under known conditions [cf. Collect. Czech. Chem. Commun., p. 729 (2000); J. Org. Chem., p. 5298 (2000); Heterocycles, p. 1173 (1987); Chem. Pharm. Bull., p. 1440 (1991)]. Compounds in which $L^1$ represents C(O)alkyl are advantageously obtained from the corresponding cyanides by reaction with Grignard or alkyllithium compounds under known conditions [cf. J. Org. Chem., p. 4844 (1994); Synthetic Commun., p. 4067 (1998); Tetrahedron Lett., p. 6505 (1988)].

The reaction mixtures are worked up conventionally, e.g. by mixing with water, separating the phases and possibly chromatographic purification of the crude products. Some of the intermediates and final products are obtained in the form of colorless or slightly brownish viscous oils which, under reduced pressure and at moderately elevated temperature, are freed or purified from volatile constituents. If the intermediates and final products are obtained as solids, the purification can also take place by recrystallization or trituration.

If individual compounds I are not accessible by the methods described above, they can be prepared by derivatization of other compounds I.

If isomeric mixtures are obtained in the synthesis, a separation is, however, generally not absolutely necessary, since the individual isomers can sometimes be converted into one another during preparation for application or upon application (e.g., under the effect of light, acid or bases). Corresponding conversions can also take place after application, for example, in the treatment of plants, in the treated plant or in the harmful fungus to be controlled.

Collective terms were used in the definitions of the symbols given in the above formulae, which collective terms are generally representative of the following substituents:

halogen: fluorine, chlorine, bromine and iodine;

alkyl: saturated, straight-chain or branched hydrocarbon radicals with 1 to 4, 6 or 8 carbon atoms, e.g. $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups with 1 to 8 carbon atoms (as mentioned above), in which the hydrogen atoms in these groups can be partially or completely replaced by halogen atoms as mentioned above, e.g. $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated, straight-chain or branched hydrocarbon radicals with 2 to 4, 6 or 8 carbon atoms and a double bond in any position, e.g. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

haloalkenyl: unsaturated, straight-chain or branched hydrocarbon radicals with 2 to 8 carbon atoms and a double bond in any position (as mentioned above), in which the hydrogen atoms in these groups can be partially or completely replaced by halogen atoms as mentioned above, in particular fluorine, chlorine and bromine;

alkynyl: straight-chain or branched hydrocarbon groups with 2 to 4, 6 or 8 carbon atoms and a triple bond in any position, e.g. $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

haloalkynyl: unsaturated, straight-chain or branched hydrocarbon radicals with 2 to 8 carbon atoms and a triple bond in any position (as mentioned above), in which the hydrogen atoms in these groups can be partially or completely replaced by halogen atoms as mentioned above, in particular fluorine, chlorine and bromine;

cycloalkyl: saturated mono- or bicyclic hydrocarbon groups with 3 to 6 or 8 carbon ring members, e.g. $C_3$–$C_8$-cycloalkyl, such as cyclopropyl, cyclobutyl, cyclopentyl, cyclohexyl, cycloheptyl and cyclooctyl;

alkoxycarbonyl: an alkoxy group with 1 to 6 carbon atoms (as mentioned above) which is bonded to the backbone via a carbonyl group (—CO—);

oxyalkylenoxy: unbranched divalent chains formed from 1 to 3 $CH_2$ groups in which both valencies is bonded to the backbone via an oxygen atom, e.g. $OCH_2O$, $OCH_2CH_2O$ and $OCH_2CH_2CH_2O$;

five- to ten-membered saturated, partially unsaturated or aromatic heterocycle comprising one to four heteroatoms from the group consisting of O, N and S:

5- or 6-membered heterocyclyl comprising one to three nitrogen atoms and/or one oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

5-membered heteroaryl comprising one to four nitrogen atoms or one to three nitrogen atoms and one sulfur or oxygen atom: 5-ring heteroaryl groups which, in addition to carbon atoms, can comprise one to four nitrogen atoms or one to three nitrogen atoms and one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl comprising one to three or one to four nitrogen atoms: 6-ring heteroaryl groups which, in addition to carbon atoms, can comprise one to three or one to four nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

alkylene: unbranched divalent chains formed from 3 to 5 $CH_2$ groups, e.g. $CH_2$, $CH_2CH_2$, $CH_2CH_2CH_2$, $CH_2CH_2CH_2CH_2$ and $CH_2CH_2CH_2CH_2CH_2$;

oxyalkylene: unbranched divalent chains formed from 2 to 4 $CH_2$ groups in which one valency is bonded to the backbone via an oxygen atom, e.g. $OCH_2CH_2$, $OCH_2CH_2CH_2$ and $OCH_2CH_2CH_2CH_2$;

oxyalkylenoxy: unbranched divalent chains formed from 1 to 3 $CH_2$ groups in which both valencies is bonded to the backbone via an oxygen atom, e.g. $OCH_2O$, $OCH_2CH_2O$ and $OCH_2CH_2CH_2O$.

The (R)- and (S)-isomers and the racemates of compounds of the formula I which have chiral centers are included in the present invention.

The embodiments of the intermediates which are especially preferred with regard to the variables correspond to those of the radicals $L^1$, $L^2$, $L^3$, $L^4$, $L^5$, $R^1$, $R^2$ and X of the formula I.

In view of their intended use of the triazolopyrimidines of the formula I, the following meanings of the substituents, in each case alone or in combination, are especially preferred:

Preference is given to compounds I in which $R^1$ is $C_1$–$C_6$-alkyl or $C_1$–$C_8$-haloalkyl.

Preference is also given to compounds I in which $R^1$ is $C_2$–$C_{10}$-alkenyl or $C_2$–$C_{10}$-alkynyl.

Preference is similarly given to compounds I in which $R^1$ is a saturated or aromatic 5- or 6-membered heterocycle.

Compounds I are particularly preferred in which $R^1$ is a group B

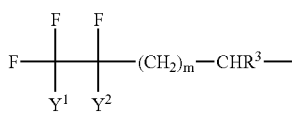

in which $Y^1$ represents hydrogen, fluorine or $C_1$–$C_6$-fluoroalkyl,
$Y^2$ represents hydrogen or fluorine, or $Y^1$ and $Y^2$ together form a double bond;
m is 0 or 1; and
$R^3$ represents hydrogen or methyl.

Preference is furthermore given to compounds I in which $R^1$ is $C_3$–$C_6$-cycloalkyl which can be substituted by $C_1$–$C_4$-alkyl.

Preference is particularly given to compounds I in which $R^2$ represents hydrogen.

Similarly preferred are compounds I in which $R^2$ is methyl or ethyl.

If $R^1$ and/or $R^2$ represent halogen-free groups with a center of chirality, the (R)-isomers are preferred. If $R^1$ and/or $R^2$ comprise haloalkyl or haloalkenyl groups with a center of chirality, the (S)-isomers are preferred.

Furthermore, particular preference is given to compounds I in which $R^1$ and $R^2$, together with the nitrogen atom to which they are bonded, form a five- or six-membered ring which can be interrupted by an atom from the group consisting of O, N and S and/or can carry one or more substituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain.

Particularly preferred are compounds I in which $R^1$ and $R^2$, together with the nitrogen atom to which they are bonded, form a 5- or 6-membered ring which optionally can exhibit a double bond and can be substituted as described above.

Particular preference is given in particular to compounds I in which $R^1$ and $R^2$, together with the nitrogen atom to which they are bonded, form a piperidine, morpholine or thiomorpholine ring, in particular a piperidinyl ring, which is optionally substituted by one to three halogen, $C_1$–$C_4$-alkyl or $C_1$–$C_4$-haloalkyl groups, in particular by 4-methyl.

Particularly preferred are furthermore compounds I in which $R^1$ and $R^2$, together with the nitrogen atom to which they are bonded, form a pyrrolidine ring which is optionally substituted by one or two halogen, $C_1$–$C_4$-alkyl or $C_1$–$C_4$-haloalkyl groups, in particular by 2-methyl.

Preferred are compounds of the formula I in which at least one $L^2$ and/or $L^3$ group does not represent hydrogen.

In addition, compounds of the formula I are preferred in which $L^1$ represents $S(=O)_nA^1$, $L^2$ represents halogen, $L^3$ and $L^4$ represent hydrogen or halogen and $L^5$ represents hydrogen. They are denoted as compounds I.1.

Similarly preferred are compounds I.1 in which $A^1$ represents hydrogen or, in particular, methyl.

Preference is given in particular to compounds I.1 in which n=0.

Preference is given to compounds I.1 in which both $L^2$ and $L^3$ represent halogen, in particular fluorine. Furthermore preferred are the compounds I.1 in which $L^2$ represents fluorine and $L^3$ represents chlorine or $L^2$ and $L^3$ both represent chlorine. $L^4$ preferably represents hydrogen.

An additional preferred embodiment of the compounds of the formula I are those in which $L^1$ represents cyano or $C(=O)A^2$. They are denoted as compounds I.2.

Particular preference is furthermore given to compounds I.2 in which $L^1$ represents $C_1$–$C_6$-alkoxycarbonyl.

Similarly particularly preferred are compounds I.2 in which $L^2$ represents halogen and $L^3$ represents halogen or hydrogen, in particular halogen.

Particular preference is also given to compounds I.2 in which $L^4$ represents hydrogen and $L^5$ represents hydrogen or methyl.

Preference is given in particular to compounds of the formulae IA and IB in which the variables have the meanings given for formula I:

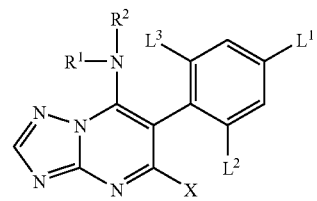

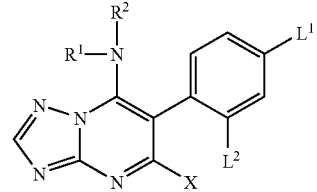

Preference is furthermore given to compounds IC:

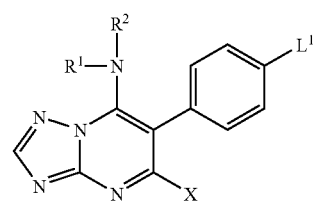

Preference is also given, in addition, to compounds I.2 in which $L^1$ represents $C(=O)OCH_3$, $L^2$ represents fluorine, $L^3$ and $L^5$ represent hydrogen and $L^4$ represents methyl.

Particular preference is given to compounds I in which X represents chlorine.

Particular preference is given, in view of their use, to the compounds I compiled in the following tables. The groups mentioned in the tables for a substituent additionally represent, considered per se, independently of the combination in which they are mentioned, a particularly preferred embodiment of the substituent in question.

Table 1

Compounds of the formula I.1 in which X represents chlorine, $L^1$ represents methylthio, $L^2$ and $L^3$ represent fluorine and $L^4$ represents hydrogen and the combination of $R^1$ and $R^2$ for a compound each time corresponds to a row of table A.

Table 2

Compounds of the formula I.1 in which X represents chlorine, $L^1$ represents methylsulfinyl, $L^2$ and $L^3$ represent fluorine and $L^4$ represents hydrogen and the combination of $R^1$ and $R^2$ for a compound each time corresponds to a row of table A.

Table 3

Compounds of the formula I.1 in which X represents chlorine, $L^1$ represents methylsulfonyl, $L^2$ and $L^3$ represent fluorine and $L^4$ represents hydrogen and the combination of $R^1$ and $R^2$ for a compound each time corresponds to a row of table A.

Table 4

Compounds of the formula I.1 in which X represents chlorine, $L^1$ represents methylthio, $L^2$ represents fluorine, $L^3$ represents chlorine and $L^4$ represents hydrogen and the combination of $R^1$ and $R^2$ for a compound each time corresponds to a row of table A.

Table 5

Compounds of the formula I.1 in which X represents chlorine, $L^1$ represents methylsulfinyl, $L^2$ represents fluorine, $L^3$ represents chlorine and $L^4$ represents hydrogen and the combination of $R^1$ and $R^2$ for a compound each time corresponds to a row of table A.

Table 6

Compounds of the formula I.1 in which X represents chlorine, $L^1$ represents methylsulfonyl, $L^2$ represents fluorine, $L^3$ represents chlorine and $L^4$ represents hydrogen and the combination of $R^1$ and $R^2$ for a compound each time corresponds to a row of table A.

Table 7

Compounds of the formula I.1 in which X represents chlorine, $L^1$ represents methylthio, $L^2$ and $L^3$ represent chlorine and $L^4$ represents hydrogen and the combination of $R^1$ and $R^2$ for a compound each time corresponds to a row of table A.

Table 8

Compounds of the formula I.1 in which X represents chlorine, $L^1$ represents methylsulfinyl, $L^2$ and $L^3$ represent chlorine and $L^4$ represents hydrogen and the combination of $R^1$ and $R^2$ for a compound each time corresponds to a row of table A.

Table 9

Compounds of the formula I.1 in which X represents chlorine, $L^1$ represents methylsulfonyl, $L^2$ and $L^3$ represent chlorine and $L^4$ represents hydrogen and the combination of $R^1$ and $R^2$ for a compound each time corresponds to a row of table A.

Table 10

Compounds of the formula IA in which X is chlorine, $L^1$ is $C(=O)OCH_3$ and $L^2$ and $L^3$ are fluorine and the combination of $R^1$ and $R^2$ for a compound each time corresponds to a row of table A.

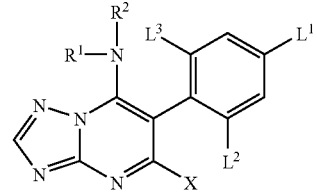

IA

Table 11

Compounds of the formula IA in which X is chlorine, $L^1$ is cyano and $L^2$ and $L^3$ are fluorine and the combination of $R^1$ and $R^2$ for a compound each time corresponds to a row of table A.

Table 12

Compounds of the formula IA in which X is chlorine, $L^1$ is CHO and $L^2$ and $L^3$ are fluorine and the combination of $R^1$ and $R^2$ for a compound each time corresponds to a row of table A.

Table 13

Compounds of the formula IA in which X is chlorine, $L^1$ is $C(=O)CH_3$ and $L^2$ and $L^3$ are fluorine and the combination of $R^1$ and $R^2$ for a compound each time corresponds to a row of table A.

Table 14

Compounds of the formula IA in which X is chlorine, $L^1$ is $C(=O)NHCH_3$ and $L^2$ and $L^3$ are [lacuna] and the combination of $R^1$ and $R^2$ for a compound each time corresponds to a row of table A.

Table 15

Compounds of the formula IB in which X is chlorine, $L^1$ is $C(=O)OCH_3$ and $L^2$ is fluorine and the combination of $R^1$ and $R^2$ for a compound each time corresponds to a row of table A.

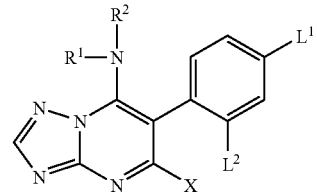

IB

Table 16

Compounds of the formula IB in which X is chlorine, $L^1$ is $C(=O)OCH_3$ and $L^2$ is chlorine and the combination of $R^1$ and $R^2$ for a compound each time corresponds to a row of table A.

Table 17

Compounds of the formula IC in which X is chlorine and $L^1$ is $C(=O)OCH_3$ and the combination of $R^1$ and $R^2$ for a compound each time corresponds to a row of table A.

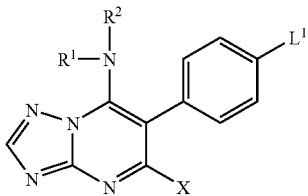

Table 18

Compounds of the formula IC in which X is chlorine and $L^1$ is cyano and the combination of $R^1$ and $R^2$ for a compound each time corresponds to a row of table A.

Table 19

Compounds of the formula I in which X is chlorine, $L^1$ is $C(=O)OCH_3$, and $L^2$, $L^3$, $L^4$ and $L^5$ are fluorine and the combination of $R^1$ and $R^2$ for a compound each time corresponds to a row of table A.

TABLE A

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CF_3$ | H |
| A-5 | $CH_2CF_3$ | $CH_3$ |
| A-6 | $CH_2CF_3$ | $CH_2CH_3$ |
| A-7 | $CH_2CCl_3$ | H |
| A-8 | $CH_2CCl_3$ | $CH_3$ |
| A-9 | $CH_2CCl_3$ | $CH_2CH_3$ |
| A-10 | $CH_2CH_2CH_3$ | H |
| A-11 | $CH_2CH_2CH_3$ | $CH_3$ |
| A-12 | $CH_2CH_2CH_3$ | $CH_2CH_3$ |
| A-13 | $CH_2CH_2CH_3$ | $CH_2CH_2CH_3$ |
| A-14 | $CH(CH_3)_2$ | H |
| A-15 | $CH(CH_3)_2$ | $CH_3$ |
| A-16 | $CH(CH_3)_2$ | $CH_2CH_3$ |
| A-17 | (±) $CH(CH_3)-CH_2CH_3$ | H |
| A-18 | (±) $CH(CH_3)-CH_2CH_3$ | $CH_3$ |
| A-19 | (±) $CH(CH_3)-CH_2CH_3$ | $CH_2CH_3$ |
| A-20 | (S) $CH(CH_3)-CH_2CH_3$ | H |
| A-21 | (S) $CH(CH_3)-CH_2CH_3$ | $CH_3$ |
| A-22 | (S) $CH(CH_3)-CH_2CH_3$ | $CH_2CH_3$ |
| A-23 | (R) $CH(CH_3)-CH_2CH_3$ | H |
| A-24 | (R) $CH(CH_3)-CH_2CH_3$ | $CH_3$ |
| A-25 | (R) $CH(CH_3)-CH_2CH_3$ | $CH_2CH_3$ |
| A-26 | (±) $CH(CH_3)-CH(CH_3)_2$ | H |
| A-27 | (±) $CH(CH_3)-CH(CH_3)_2$ | $CH_3$ |
| A-28 | (±) $CH(CH_3)-CH(CH_3)_2$ | $CH_2CH_3$ |
| A-29 | (S) $CH(CH_3)-CH(CH_3)_2$ | H |
| A-30 | (S) $CH(CH_3)-CH(CH_3)_2$ | $CH_3$ |
| A-31 | (S) $CH(CH_3)-CH(CH_3)_2$ | $CH_2CH_3$ |
| A-32 | (R) $CH(CH_3)-CH(CH_3)_2$ | H |
| A-33 | (R) $CH(CH_3)-CH(CH_3)_2$ | $CH_3$ |
| A-34 | (R) $CH(CH_3)-CH(CH_3)_2$ | $CH_2CH_3$ |
| A-35 | (±) $CH(CH_3)-C(CH_3)_3$ | H |
| A-36 | (±) $CH(CH_3)-C(CH_3)_3$ | $CH_3$ |
| A-37 | (±) $CH(CH_3)-C(CH_3)_3$ | $CH_2CH_3$ |
| A-38 | (S) $CH(CH_3)-C(CH_3)_3$ | H |
| A-39 | (S) $CH(CH_3)-C(CH_3)_3$ | $CH_3$ |
| A-40 | (S) $CH(CH_3)-C(CH_3)_3$ | $CH_2CH_3$ |
| A-41 | (R) $CH(CH_3)-C(CH_3)_3$ | H |
| A-42 | (R) $CH(CH_3)-C(CH_3)_3$ | $CH_3$ |
| A-43 | (R) $CH(CH_3)-C(CH_3)_3$ | $CH_2CH_3$ |
| A-44 | (±) $CH(CH_3)-CF_3$ | H |
| A-45 | (±) $CH(CH_3)-CF_3$ | $CH_3$ |
| A-46 | (±) $CH(CH_3)-CF_3$ | $CH_2CH_3$ |
| A-47 | (S) $CH(CH_3)-CF_3$ | H |
| A-48 | (S) $CH(CH_3)-CF_3$ | $CH_3$ |
| A-49 | (S) $CH(CH_3)-CF_3$ | $CH_2CH_3$ |
| A-50 | (R) $CH(CH_3)-CF_3$ | H |

TABLE A-continued

| No. | $R^1$ | $R^2$ |
|---|---|---|
| A-51 | (R) $CH(CH_3)-CF_3$ | $CH_3$ |
| A-52 | (R) $CH(CH_3)-CF_3$ | $CH_2CH_3$ |
| A-53 | (±) $CH(CH_3)-CCl_3$ | H |
| A-54 | (±) $CH(CH_3)-CCl_3$ | $CH_3$ |
| A-55 | (±) $CH(CH_3)-CCl_3$ | $CH_2CH_3$ |
| A-56 | (S) $CH(CH_3)-CCl_3$ | H |
| A-57 | (S) $CH(CH_3)-CCl_3$ | $CH_3$ |
| A-58 | (S) $CH(CH_3)-CCl_3$ | $CH_2CH_3$ |
| A-59 | (R) $CH(CH_3)-CCl_3$ | H |
| A-60 | (R) $CH(CH_3)-CCl_3$ | $CH_3$ |
| A-61 | (R) $CH(CH_3)-CCl_3$ | $CH_2CH_3$ |
| A-62 | $CH_2CF_2CF_3$ | H |
| A-63 | $CH_2CF_2CF_3$ | $CH_3$ |
| A-64 | $CH_2CF_2CF_3$ | $CH_2CH_3$ |
| A-65 | $CH_2(CF_2)_2CF_3$ | H |
| A-66 | $CH_2(CF_2)_2CF_3$ | $CH_3$ |
| A-67 | $CH_2(CF_2)_2CF_3$ | $CH_2CH_3$ |
| A-68 | $CH_2C(CH_3)=CH_2$ | H |
| A-69 | $CH_2C(CH_3)=CH_2$ | $CH_3$ |
| A-70 | $CH_2C(CH_3)=CH_2$ | $CH_2CH_3$ |
| A-71 | $CH_2CH=CH_2$ | H |
| A-72 | $CH_2CH=CH_2$ | $CH_3$ |
| A-73 | $CH_2CH=CH_2$ | $CH_2CH_3$ |
| A-74 | $CH(CH_3)CH=CH_2$ | H |
| A-75 | $CH(CH_3)CH=CH_2$ | $CH_3$ |
| A-76 | $CH(CH_3)CH=CH_2$ | $CH_2CH_3$ |
| A-77 | $CH(CH_3)C(CH_3)=CH_2$ | H |
| A-78 | $CH(CH_3)C(CH_3)=CH_2$ | $CH_3$ |
| A-79 | $CH(CH_3)C(CH_3)=CH_2$ | $CH_2CH_3$ |
| A-80 | cyclopentyl | H |
| A-81 | cyclopentyl | $CH_3$ |
| A-82 | cyclopentyl | $CH_2CH_3$ |
| A-83 | cyclohexyl | H |
| A-84 | cyclohexyl | $CH_3$ |
| A-85 | cyclohexyl | $CH_2CH_3$ |
| A-86 | $-(CH_2)_2CH=CHCH_2-$ | |
| A-87 | $-(CH_2)_2C(CH_3)=CHCH_2-$ | |
| A-88 | $-(CH_2)_2CH(CH_3)(CH_2)_2-$ | |
| A-89 | $-(CH_2)_2CHF(CH_2)_2-$ | |
| A-90 | $-(CH_2)_3CHFCH_2-$ | |
| A-91 | $-(CH_2)_2CH(CF_3)(CH_2)_2-$ | |
| A-92 | $-(CH_2)_2O(CH_2)_2-$ | |
| A-93 | $-(CH_2)_2S(CH_2)_2-$ | |
| A-94 | $-(CH_2)_5-$ | |
| A-95 | $-(CH_2)_4-$ | |
| A-96 | $-CH_2CH=CHCH_2-$ | |
| A-97 | $-CH(CH_3)(CH_2)_3-$ | |
| A-98 | $-CH_2CH(CH_3)(CH_2)_2-$ | |

The compounds I are suitable as fungicides. They are distinguished by an outstanding effectiveness against a broad spectrum of phytopathogenic fungi, especially from the classes of the *Ascomycetes, Deuteromycetes, Phycomycetes* and *Basidiomycetes*. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,

*Botrytis cinerea* (gray mold) on strawberries, vegetables, ornamental plants and grapevines,

*Cercospora arachidicola* on peanuts,

*Erysiphe cichoracearum* and *Sphaerotheca fuliginea* on cucurbits,

*Blumeria graminis* (powdery mildew) on cereals,

*Fusarium* and *Verticillium* species on various plants,
*Helminthosporium* species on cereals,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi. The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the effect desired. Amounts customarily applied in the protection of materials are, for example, 0.001 g to 2 kg, preferably 0.005 g to 1 kg, of active compound per cubic meter of treated material.

The compounds I can be converted to the usual formulations, e.g. solutions, emulsions, suspensions, dusts, powders, pastes and granules. The application form depends on the respective use intended; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalensulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel fuel, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, combinations for broadcasting and dusts can be prepared by mixing or mutually grinding the active substances with a solid carrier.

Granules, e.g. coated granules, impregnated granules and homogeneous granules, can be prepared by binding the active compounds to solid carriers. Solid carriers are, e.g., mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

Examples for formulations are:

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecylbenzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are intimately mixed with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100 000 parts by weight of water and finely dispersing it therein, an aqueous dispersion is obtained comprising 0.02% by weight of the active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20 000 parts by weight of water.

The active compounds can be used as such, in the form of their formulations or of the application forms prepared therefrom, e.g. in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; they should in any case guarantee the finest possible dispersion of the active compounds according to the invention.

Aqueous application forms can be prepared from emulsion concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, concentrates comprising active substance, wetting agent, tackifier, dispersant or emulsifier and possibly solvent or oil can also be prepared, which concentrates are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra low volume (ULV) process, it being possible to apply formulations with more than 95% by weight of active compound or even the active compound without additives.

Oils of various types, herbicides, fungicides, other pesticides and bactericides can be added to the active compounds, if need be also not until immediately before use (tank mix). These agents can be added to the compositions according to the invention in a weight ratio of 1:10 to 10:1.

The compositions according to the invention can, in the application form as fungicides, also be present together with other active compounds, which e.g. with herbicides, insecticides, growth regulators, fungicides or also with fertilizers. On mixing the compounds I or the compositions comprising them in the application form as fungicides with other fungicides, in many cases an expansion of the fungicidal spectrum of activity is obtained.

The following list of fungicides, with which the compounds according to the invention can be used in conjunction, is intended to illustrate the possible combinations but does not limit them:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate) or N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate or diisopropyl 5-nitroisophthalate;

heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-(methoxycarbonylamino) benzimidazole, 2-(2-furyl)benzimidazole, 2-(4-thiazolyl) benzimidazole, N-(1,1,2,2-tetrachloroethylthio) tetrahydrophthalimide, N-(trichloromethylthio) tetrahydrophthalimide or N-(trichloromethylthio) phthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazin-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-(tert-butyl)phenyl)-2-methylpropyl]-cis-2,6-dimethyl-morpholine, N-[3-(p-(tert-butyl)phenyl)-2-methyl propyl] piperidine, 1-[2-(2,4-dichlorophenyl)-4-ethyl-1,3-dioxolan-2-ylethyl]-1H-1,2,4-triazole, 1-[2-(2,4-dichlorophenyl)-4-(n-propyl)-1,3-dioxolan-2-yl-ethyl]-1H-1,2,4-triazole, N-(n-propyl)-N-(2,4,6-trichlorophenoxyethyl)-N'-imidazolylurea, 1-(4- chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene or 1,2-bis(3-methoxycarbonyl-2-thioureido)benzene, strobilurins, such as methyl E-methoxyimino[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]-acetamide, methyl-E-methoxyimino[α-(2,5-dimethylphenoxy)-o-tolyl]acetamide, methyl E-2-{2-[2-trifluoromethylpyrid-6-yl]oxymethyl]phenyl}-3-methoxyacrylate, methyl(E,E)-methoxy imino{2-[1-(3-trifluoromethylphenyl)ethylideneaminooxymethyl]phenyl}acetate or methyl N-(2-{[1-(4-chlorophenyl)-1H-pyrazol-3-yl]oxymethyl}phenyl)-N-methoxycarbamate, anilinopyrimidines, such as N-(4,6-dimethylpyrimidin-2-yl)aniline, N-[4-methyl-6-(1-propynyl)pyrimidin-2-yl]aniline or N-[4-methyl-6-cyclopropylpyrimidin-2-yl]aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloylmorpholine or 3-(4-fluorophenyl-3-(3,4-dimethoxyphenyl)acryloylmorpholine, and various fungicides, such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl glutarimide, hexachlorobenzene, methyl N-(2,6-dimethylphenyl)-N-(2-furoyl)-DL-alaninate, N-(2,6-dimethylphenyl)-N-(2'-methoxyacetyl)-DL-alanine methyl ester, N-(2,6-dimethylphenyl)-N-chloroacetyl-D,L-2-aminobutyro-lactone, N-(2,6-dimethylphenyl)-N-(phenylacetyl)-DL-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarba-moylhydantoin, N-(3,5-dichlorophenyl)-1,2-dimethylcyclopropane-1,2-dicarboximide, 2-cyano-[N-(ethylaminocarbonyl)-2-methoxyimino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, 5-chloro-2-cyano-4-(p-tolyl)imidazole-1-sulfonic acid dimethylamide or 3,5-dichloro-N-(3-chloro-1-ethyl-1-methyl-2-oxopropyl)-4-methylbenzamide.

SYNTHESIS EXAMPLES

The procedures described in the following synthesis examples were used to prepare further compounds I by appropriate modification of the starting compounds. The compounds thus obtained are listed in the following table, together with physical data.

Example 1

Preparation of Diethyl 4-cyanophenylmalonate

Diethyl malonate (0.49 mol) was added at approximately 60° C. over 2 hours to a suspension of sodium hydride (0.51 mol) in 140 ml of 1,4-dioxane. After stirring for a further 10 min, 0.05 mol of CuBr were added. After 15 min, 0.25 mol of 4-cyanobromobenzene in 10 ml of dioxane were added. The reaction mixture was maintained at 100° C. for approximately 14 hours and then, at approximately 15° C., 35 ml of 12N hydrochloric acid were slowly added. The precipitate was filtered off and the filtrate was extracted with diethyl ether. After phase separation, the organic phase was dried and then freed from the solvent. 32 g of the title compound remained.

Example 2

Preparation of 5,7-dihydroxy-6-(4-cyanophenyl)-[1,2,4]triazolo[1,5-a]pyrimidine

A mixture of 14 g of 3-amino-1,2,4-triazole, 0.17 mol of the ester from example 1 and 50 ml of tributylamine (50 ml) was stirred at 180° C. for approximately 6 hours. A solution of 21 g of NaOH in 200 ml of water was added at approximately 700 and the mixture was stirred for a further 30 min. The organic phase was separated and the aqueous phase was extracted with diethyl ether. The product precipitated from the aqueous phase after acidification with concentrated hydrochloric acid. 28 g of the title compound were obtained by filtration.

Example 3

Preparation of 5,7-dichloro-6-(4-cyanophenyl)-[1,2,4]triazolo[1,5-a]pyrimidine

A mixture of 25 g of the triazolopyrimidine from example 2 and 50 ml of $POCl_3$ was refluxed for 8 hours, $POCl_3$ being distilled off. The residue was added to a $CH_2Cl_2$-water mixture and the organic phase was separated, washed, dried and then freed from the solvent. 23 g of the title compound were obtained.

Example 4

Preparation of 5-chloro-6-(4-cyanophenyl)-7-isopropylamino-[1,2,4]triazolo [1,5-a]pyrimidine [I-1]

A solution of 1.5 mmol of isopropylamine and 1.5 mmol of triethylamine in 10 ml of dichloromethane was added with stirring to a solution of 1.5 mmol of the product from ex. 3 in 20 ml of dichloromethane. The reaction mixture was stirred at 20 to 25° C. for approximately 16 hours and then washed with dilute hydrochloric acid. The organic phase was separated, dried and freed from the solvent. After chromatography on silica gel, 330 mg of the title compound with a melting point of 190° C. were obtained.

Example 5

Preparation of 5,7-dihydroxy-6-(2,6-difluoro-4-thiomethylphenyl)-[1,2,4]triazolo[1,5-a]pyrimidine A mixture of 3-amino-1,2,4-triazole (14 g), diethyl(2,6-difluoro-4-(thiomethyl)phenyl)malonate (0.17 mol) and tributylamine (50 ml) was heated at 180° C. for approximately 6 hours. After cooling the reaction mixture to 70° C., the solution was treated with 21 g of NaOH in 200 ml of water and stirred for a further 30 min. After separating the organic phase and extracting the aqueous phase with diethyl ether, the title compound was precipitated from the aqueous phase by acidification with concentrated HCl solution. 37 g were isolated.

Example 6

Preparation of 5,7-dichloro-6-(2,6-difluoro-4-(thiomethyl)phenyl)-[1,2,4]triazolo 1,5-a]pyrimidine A mixture of 5,7-dihydroxy-6-(2,6-difluoro-4-(thiomethyl)phenyl)-[1,2,4]triazolo[1,5-a]pyrimidine (30 g, Ex. 5) and 50 ml of $POCl_3$ was refluxed for approximately eight hours; some $POCl_3$ was distilled off in the process. The residue was added to a $CH_2Cl_2$/water mixture. The organic phase was separated, dried and freed from the solvent. 21 g of the title compound with a melting point of 138° C. remained behind.

Example 7

Preparation of 5-chloro-6-(2,6-difluoro-4-(thiomethyl)phenyl)-7-(1,1,1-trifluoroprop-2-yl)amino-[1,2,4]triazolo[1,5-a]pyrimidine [1–6]

A solution of 6 mmol of 5,7-dichloro-6-(2,6-difluoro-4-(thiomethyl)phenyl)-[1,2,4]triazolo[1,5-a]pyrimidine (Ex. 6) in 20 ml of dichloromethane was treated, with stirring, with a solution of 6 mmol of 1,1,1-trifluoro-2-aminopropane and 6 mmol of triethylamine in 40 ml of dichloromethane. The solution was stirred at 20–25° C. for approximately 16 hours and then was washed with dilute HCl solution. The organic phase was separated, dried and freed from the solvent. After chromatography on silica gel, 1.2 g of the title compound with a melting point of 174° C. were obtained from the residue.

Example 8

Preparation of 5-chloro-6-(2,6-difluoro-4-(methylsulfonyl)phenyl)-7-(1,1,1-trifluoroprop-2-yl)amino-[1,2,4]triazolo[1,5-a]pyrimidine (8a) and 5-chloro-6-(2,6-difluoro-4-(methylsulfinyl)phenyl)-7-(1,1,1-trifluoroprop-2-yl)amino-[1,2,4]triazolo[1,5-a] pyrimidine (8b)

A solution of 3 mmol of 5-chloro-6-(2,6-difluoro-4-(thiomethyl)phenyl)-7-(1,1,1-trifluoroprop-2-yl)amino-[1,2,4] triazolo[1,5-a]pyrimidine (Ex. 7) in 20 ml of dichloromethane was treated with 0.13 g of ammonium molybdate and 0.22 ml of 98% formic acid. 9 mmol of $H_2O_2$ were added and then the reaction mixture was stirred at 20–25° C. for 24 hours. The reaction mixture was added to water and the organic phase was separated, washed with 10% $NaHSO_3$ solution, dried and freed from the solvent. After chromatography on silica gel, 0.28 g of the sulfone (8a) with a melting point of 211° C. and 0.39 g of the sulfoxide (8b) with a melting point of 264° C. were obtained.

Example 9

Preparation of 5-cyano-6-(2,6-difluoro-4-cyanophenyl)-7-(4-methylpiperidin-1-yl)-[1,2,4]triazolo[1,5-a]pyrimidine A mixture of 0.1 mol of 5-chloro-6-(2,6-difluoro-4-cyanophenyl)-7-(4-methylpiperidin-1-yl)-[1,2,4]-triazolo-[1,5-a]-pyrimidine (No. I-5) and 0.25 mol of tetraethylammonium cyanide in 750 ml of dimethylformamide (DMF) was stirred at 20–25° C. for 16 hours. After addition of water and methyl tert-butyl ether (MTBE), the organic phase was separated, washed with water, dried and freed from the solvent. After chromatography on silica gel, 6.33 g of the title compound were obtained from the residue.

$^1H$ NMR: 8.55 (s), 7.45 (d), 3.80 (d), 2.95 (t), 1.70 (m), 1.65 (m), 1.40 (m), 0.98 (d).

Example 10

Preparation of 5-methoxy-6-(2,6-difluoro-4-cyanophenyl)-7-(4-methylpiperidin-1-yl)-[1,2,4]triazolo[1,5-a]pyrimidine A solution of 65 mmol of compound I-5 in 400 ml of anhydrous methanol was, after addition of 71.5 mmol of a 30% sodium methoxide solution at 20–25° C., stirred at this temperature for approximately 16 hours. Methanol was distilled off and the residue was taken up in dichloromethane, then washed with water and, after drying, freed from the solvent. After chromatography on silica gel, 3.68 g of the title compound were obtained from the residue.

$^1H$ NMR: 8.75 (s), 7.35 (d), 3.95 (s), 3.65 (d), 2.70 (t), 1.65 (m), 1.55 (m), 1.45 (m), 0.95 (d).

Example 11

Preparation of 5-methyl-6-(2,6-difluoro-4-cyanophenyl)-7-(4-methylpiperidin-1-yl)-[1,2,4]triazolo[1,5-a]pyrimidine A mixture of 20 ml of diethyl malonate and 0.27 g (5.65 mmol) of NaH (50% dispersion in mineral oil) in 50 ml of acetonitrile was stirred at 20–25° C. for approximately 2 hours. 4.71 mmol of compound I-5 were added to this mixture and then the mixture was heated to approximately 60° C. and stirred at this temperature for 20 hours. After addition of 50 ml of aqueous $NH_4Cl$ solution, the acidification was carried out with dilute HCl. After extracting with MTBE, the combined organic phases were dried and evaporated. The residue was purified by chromatography on silica gel. The pure product was taken up in concentrated HCl and held at 80° C. for 24 hours. After cooling the reaction mixture, the pH was adjusted to 5 by addition of aqueous NaOH solution and then the mixture was extracted with MTBE. The combined organic phases were, after drying, freed from the solvent. After chromatography on silica gel, 0.78 g of the title compound was obtained from the residue.

$^1H$ NMR: 8.75 (s), 7.35 (d), 3.65 (d), 2.70 (t), 2.43 (s), 1.65 (m), 1.55 (m), 1.45 (m), 0.95 (d).

Example 12

Preparation of 5-chloro-6-(2,6-difluoro-4-carboxaldehydephenyl)-7-(4-methylpiperidin-1-yl)-[1,2,4]triazolo[1,5-a]pyrimidine A solution of 1.5 mmol of compound I-5 in 20 ml of dichloromethane was treated at 0° C. with a 1M solution of 1.65 mmol of diisobutylaluminum hydride (DIBAH) in dichloromethane and was stirred at 20–25° C. for 2 hours. This mixture was treated with saturated NH$_4$Cl solution and 10% HCl solution and the organic phase was separated and washed with water. After drying, the solvent was removed and, after chromatography on silica gel, 0.36 g of the title compound was obtained from the residue.

$^1$H NMR: 10.05 (s), 8.40 (s), 7.60 (d), 3.70 (d), 2.85 (t), 1.65 (m), 1.55 (m), 1.40 (m), 0.95 (d).

Example 13

Preparation of 5-chloro-6-(2,6-difluoro-4-acetylphenyl)-7-(4-methylpiperidin-1-yl)-[1,2,4]triazolo[1,5-a]pyrimidine A solution of 1.5 mmol of compound I-5 in 20 ml of tetrahydrofuran (THF) was treated, at 20–25° C., with 1.65 mmol of CuBr and a 3M solution of 1.65 mmol of methylmagnesium chloride in THF and the mixture was stirred for approximately 30 min. This mixture was treated with saturated NH$_4$Cl solution and 10% HCl solution and the organic phase was separated and washed with water. After drying, the solvent was removed and, after chromatography on silica gel, 0.22 g of the title compound was obtained from the residue.

$^1$H NMR: 8.40 (s), 7.65 (d), 3.70 (d)., 2.80 (t), 2.70 (s), 1.70 (m), 1.55 (m), 1.40 (m), 0.98 (d).

Examples for the Action Against Harmful Fungi

The fungicidal action of the compounds of the general formula I can be demonstrated from the following tests:

The active compounds were prepared, separately or together, as a 10% emulsion in a mixture of 70% by weight of cyclohexanone, 20% by weight of Nekanil® LN (Lutensol® AP6, wetting agent with an emulsifying and dispersing action based on ethoxylated alkylphenols) and 10% by weight of Wettol® EM (nonionic emulsifier based on ethoxylated castor oil) and were appropriately diluted with water to the desired concentration.

Use Example 1

Activity Against Early Blight of Tomato Caused by *Alternaria solani*

Leaves of pot plants of the variety "Große Fleischtomate St. Pierre" were sprayed to runoff point with an aqueous suspension prepared from a stock solution consisting of 10% of active compound, 85% of cyclohexanone and 5% of emulsifier. On the following day, the leaves were infected with an aqueous suspension of zoospores of *Alternaria solani* in 2% Biomalz solution with a concentration of 0.17×10$^6$ spores/ml. The plants were subsequently placed in a chamber saturated with water vapor at temperatures between 20 and 22° C. After 5 days, early blight in the untreated but infected control plants had so extensively developed that the infection could be visually determined in %.

In this test, the plants treated with 63 ppm of the active compound I-2 of table I showed no infection, while the untreated plants were 90% infected.

TABLE I

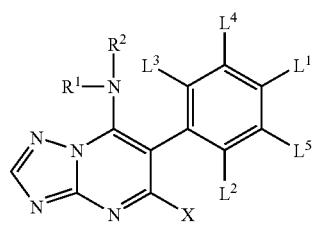

| No. | R$^1$ | R$^2$ | L$^1$ | L$^2$ | L$^3$ | L$^4$ | L$^5$ | X | Phys. data (M.p. [° C.]) |
|---|---|---|---|---|---|---|---|---|---|
| I-1 | CH(CH$_3$)$_2$ | H | CN | H | H | H | H | Cl | 190 |
| I-2 | —(CH$_2$)$_2$CH(CH$_3$)(CH$_2$)$_2$— | | COOCH$_3$ | F | F | H | H | Cl | 8.7(s), 7.8(d), 3.9(s), 3.7(d), 2.8(t), 1.6(m), 1.2(m), 0.9(d) |
| I-3 | cyclopentyl | H | CN | H | H | H | H | Cl | 207 |
| I-4 | CH(CH$_3$)C(CH$_3$)$_3$ | H | CN | H | H | H | H | Cl | 130 |
| I-5 | —(CH$_2$)$_2$CH(CH$_3$)(CH$_2$)$_2$— | | CN | F | F | H | H | Cl | 8.4(s), 7.4(d), 3.7(d), 2.8(t), 1.7(m), 1.4(m), 0.9(d) |
| I-6 | CH(CH$_3$)—CF$_3$ | H | SCH$_3$ | F | F | H | H | Cl | 174 |
| I-7 | CH(CH$_3$)—CF$_3$ | H | SCH$_3$ | F | H | F | H | Cl | 164 |
| I-8 | CH$_2$CF$_3$ | H | SCH$_3$ | F | H | F | H | Cl | 161 |

In the case of chiral R$^1$ groups, because of the hindered rotation of the phenyl group, two diastereoisomers A) and B) may exist, which may differ in their physical properties.

Use Example 2

Activity Against Net Blotch of Barley Caused by *Pyrenophora teres*

Leaves of pot-grown barley seedlings of the variety "Igri" were sprayed to runoff point with an aqueous preparation of active compound prepared from a stock solution consisting of 10% of active compound, 85% of cyclohexanone and 5% of emulsifier. 24 hours after the spray coating had dried on, the leaves were inoculated with an aqueous suspension of spores of *Pyrenophora* [syn. *Drechslera] teres*, the causative agent of net blotch. The test plants were subsequently placed in a greenhouse at temperatures of between 20 and 24° C. and a relative atmospheric humidity of 95 to 100%. After 6 days, the extent of development of the disease was determined visually in % of infection of the total leaf area.

In this test, the plants treated with 16 ppm of the active compound I-2 of table I showed 1% infection, while the untreated plants were 85% infected.

Use Example 3

Activity Against Early Blight of Tomato Caused by *Alternaria solani*

Pot plants of the variety "Pixie II" in the 2–4-leaf stage were sprayed to runoff point with an aqueous suspension which comprised the active compound in the concentration given below and which was prepared from a stock solution of 5% of active compound, 94% of cyclohexanone and 1% of emulsifier (Tween 20). After the leaves had dried (3 to 5 hours), they were infected with an aqueous suspension of zoospores of *Alternaria solani* comprising $0.15 \times 10^3$ spores/ml. The plants were subsequently placed in a chamber saturated with water vapor at temperatures between 22 and 24° C. for 36 hours and then in a greenhouse at a relative humidity of 95% at temperatures between 21 and 23° C. for 2 to 3 days. The extent of the development of infection on the leaf undersides was then determined visually.

In this test, the plants treated with 200 ppm of the active compounds No. I-6, I-7 and I-8 showed no infection in excess of 7%, while the untreated plants were 100% infected.

Use Example 4

Activity Against *Rhizoctonia solani* on Rice

Pot plants of the variety "M-202" in the 2-leaf stage were sprayed to runoff point with an aqueous preparation of active compound prepared with a stock solution of 5% of active compound, 94% of cyclohexanone and 1% of emulsifier (Tween 20>). After the leaves had dried (3 to 5 hours), they were inoculated, 4 ml of an aqueous mycelium suspension of *Rhizoctonia solani* being pipetted onto the soil surface of each and every pot. The plants were subsequently placed in a chamber saturated with water vapor at temperatures between 22 und 24° C. for 36 hours and then in a greenhouse at a relative humidity of 95% at temperatures between 21 and 23° C. for 2 to 3 days. The extent of the development of infection on the leaf undersides was then determined visually. The test plants were subsequently placed in climatic chambers at 18–28° C. and high atmospheric humidity for 4–5 days. The extent of the development of infection on the leaves was then determined visually.

In this test, the plants treated with 200 ppm of the active compounds No. I-6, I-7 and I-8 did not show more than 7% infection, while the untreated plants were 100% infected.

We claim:

1. A method for the control of harmful fungi, which comprises treating the fungi or the materials, plants, ground or seeds to be protected from fungal attack with an effective amount of a triazolopyrimidine of the formula I

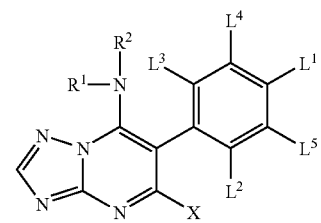

in which substituents have the following meanings:
$L^1$ is cyano, $S\{O\}_n A^1$ or $C(=O)A^2$, wherein
  $A^1$ is hydrogen, hydroxyl, $C_1$–$C_8$-alkyl, $C_1$–$C_8$-alkylamino or di($C_1$–$C_8$-alkyl)amino;
  $A^2$ is $C_1$–$C_8$-alkoxy, $C_1$–$C_6$-haloalkoxy or one of the groups mentioned under $A^1$;
n 0, 1 or 2;
$L^2$, $L^3$ are hydrogen or halogen;
$L^4$, $L^5$ are hydrogen, halogen or $C_1$–$C_4$-alkyl;
X is halogen, cyano, $C_1$–$C_4$-alkyl, $C_1$–$C_4$-haloalkyl, $C_1$–$C_4$-alkoxy or $C_1$–$C_2$-haloalkoxy;
$R^1$ is $C_1$–$C_8$-alkyl, $C_1$–$C_8$haloalkyl, $C_3$–$C_6$cycloalkyl, $C_3$–$C_6$-halocyoloalkyl, $C_2$–$C_8$-alkenyl, $C_4$–$C_{10}$-alkadienyl, $C_2$–$C_8$-haloalkenyl, $C_3$–$C_6$-cycloalkenyl, $C_2$–$C_8$-alkynyl, $C_2$–$C_8$-haloalkynyl or $C_3C_6$-cycloalkynyl, phenyl, naphthyl, or a five- to ten-membered saturated, partially unsaturated or aromatic hetero cycle, comprising one to four heteroatoms from the group consisting of O, N and S;
$R^2$ is hydrogen or one of the groups mentioned under $R^1$,
$R^1$ and $R^2$ can also, together with the nitrogen atom to which they are bonded, form a five- or aix-membered ring which can be interrupted by an atom from the group consisting of O, N and S and/or can carry one or more subatituents from the group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1C_4$-alkylene chain;
wherein $R^1$ and/or $R^2$ can be substituted by one to four identical or different groups $R^a$:
$R^a$ is halogen, cyano, nitro, hydroxyl, $C_1C_6$-alkyl, $C_1$–$C_6$haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylanino, di($C_1$–$C_6$-alkyl)amino, $C_2$–$C_6$-alkenyl, $C_2$–$C_6$-alkenyloxy, $C_3$–$C_6$alkynyloxy, $C_3$–$C_6$-cycloalkyl, phenyl, naphthyl or a five- to ten-membered saturated, partially unsaturated or aromatic heterocycle, comprising one to four heteroatoms from the group consisting of O, N and S,
wherein these aliphatic, alicyclic or aromatic groups, for their part, can be partially or completely halogenated or can carry one to three groups $R^b$:
$R^b$ is halogen, cyano, nitro, hydroxyl, mercapto, amino, carboxyl, aminocarbonyl, aminothiocarbonyl, alkyl, haloalkyl, alkenyl, alkenyloxy, alkcynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl or dialkylamincarbonyl, wherein the alkyl groups in these radicals comprise 1 to 6 carbon atoms and the alkenyl or alkynyl groups mentioned in these radicals comprise 2 to 8 carbon atoms;

and/or one to three of the following radicals:

cycloalkyl, cycloalkoxy, heterocyclyl or hetarocycyloxy, wherein the cyclic systems comprise 3 to 10 ring members; aryl, aryloxy, arylthio, aryl-$C_1$–$C_6$-alkoxy, aryl-$C_1$–$C_6$-alkyl, hetaryl, hetaryloxy or hetarylthio, wherein the aryl radicals preferably comprise 6 to 10 ring members and the hetaryl radicals comprise 5 or 6 ring members, wherein the cyclic systems can be partially or completely halogenated or can be substituted by alkyl or haloalkyl groups.

2. A triazolopyrimidine of the formula I

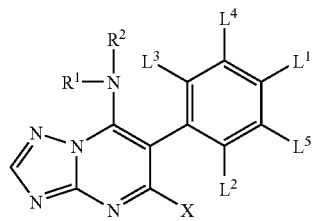

I in which substituents have the following meanings:

$L^1$ is cyano or C(=O)$A^2$, wherein
  $A^2$ is hydrogen, hydroxyl, $C_1$–$C_8$-alkyl, $C_1$–$C_8$-alkoxy, $C_1C_6$haloalkoxy, $C_1$–$C_8$-alkylamino or di($C_1$–$C_8$-alkyl)amino;

$L^2$, $L^3$ are hydrogen or halogen;

$L^4$, $L^5$ are hydrogen, halogen or $C_1$–$C_4$-alkyl;

X is halogen, cyano, $C_1$–$C_4$-alkyl, $C_1$–$C_4$-haloalkyl, $C_1$–$C_4$-alkoxy or $C_1$–$C_2$haloalkoxy;

$R^1$ is $C_1$–$C_8$-alkyl, $C_1$–$C_6$-haloalkyl, $C_3$–$C_6$-cycloalkyl $C_3$–$C_6$halocycloalkyl, $C_2$–$C_8$-alkenyl, $C_4$–$C_{10}$-alkadienyl, $C_2C_8$-haloalkenyl, $C_3$–$C_6$-cycloalkenyl, $C_2$–$C_8$-alkynyl, $C_2C_8$-haloalkynyl or $C_3$–$C_6$-cycloalkynyl, phenyl, naphthyl, or a five- to ten-membered saturated, partially unsaturated or aromatic heterocycle, comprising one to four heteroatoms from the group consisting of O, N and S;

$R^2$ is hydrogen or one of the groups mentioned under $R^1$, $R^1$ and $R^2$ can also, together with the nitrogen atom to which they are bonded, form a five- or six-membered ring which can be interrupted by an atom from the group consisting of O, N and S and/or can carry one or more substituents from group consisting of halogen, $C_1$–$C_6$-alkyl, $C_1$–$C_6$-haloalkyl and oxy-$C_1$–$C_3$-alkylenoxy or in which an N and a neighboring C atom can be connected via a $C_1$–$C_4$-alkylene chain;

wherein $R^1$ and/or $R^2$ can be substituted by one to four identical or different groups $R^a$:

$R^a$ is halogen, cyano, nitro, hydroxyl, $C_1$–$C_6$alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$alkylthio, $C_1$–$C_6$-alkylamino, di($C_1$–$C_6$-alkyl)amino, $C_2$–$C_6$-alkenyl, $C_2$–$C_6$-alkenyloxy, $C_3$–$C_6$-alkynyloxy, $C_3$–$C_6$-cycloalkyl, phenyl, naphthyl or a five- to ten-membered saturated, partially unsaturated or aromatic heterocycle, comprising one to four heteroatoms from the group consisting of O, N and S, wherein these aliphatic, alicyclic or aromatic groups, for their part, can be partially or completely halogenated or can carry one to three groups $R^b$:

$R^b$ is halogen, cyano, nitro, hydroxyl, mercapto, amino, carboxyl, aminocarbonyl, aminocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl or dialkylaminothiocarbonyl, wherein the alkyl groups in these radicals comprise 1 to 6 carbon atoms and the alkenyl or alkynyl groups mentioned in these radicals comprise 2 to 8 carbon atoms;

and/or one to three of the following radicals:

cycloalkyl, cycloalkoxy, heterocyclyl or heterocycyloxy, wherein the cyclic systems comprise 3 to 10 ring members; aryl, aryloxy, arylthio, aryl-$C_1$–$C_6$-alkoxy, aryl-$C_1$–$C_6$-alkyl, hetaryl, hetaryloxy or hetarylthio, wherein the aryl radicals preferably comprise 6 to 10 ring members and the hetaryl radicals comprise 5 or 6 ring members, wherein the cyclic systems can be partially or completely halogenated or can be substituted by alkyl or haloalkyl groups.

3. A compound of the formula I as claimed in claim 2, in which $L^2$ represents halogen;

$L^3$, $L^4$ represent hydrogen or halogen; and $L^5$ represents hydrogen.

4. A compound of the formula I as claimed in claim 2, in which X represents halogen.

5. A compound of the formula I as claimed in claim 2, in which $R^1$ and $R^2$ have the following meanings:

$R^1$ is $C_1$–$C_6$-alkyl, $C_1$–$C_8$-haloalkyl, $C_3$–$C_6$-cycloalkyl, $C_3$–$C_6$-halocycloalkyl, $C_2$–$C_8$-alkenyl, $C_2$–$C_8$haloalkenyl, $C_2$–$C_8$-alkynyl; and $R^2$ is hydrogen or $C_1$–$C_4$-alkyl; or $R^1$ and $R^2$ can also, together with the nitrogen atom to which they are bonded, form a saturated or unsaturated 5- or 6-membered ring which can carry one or two substituents from the group consisting of halogen, $C_1$–$C_6$-alkyl and $C_1$–$C_6$-haloalkyl.

6. A process for the preparation of the compounds of the formula I as claimed in claim 2 in which X is halogen, cyano, $C_1$–$C_4$-alkoxy or $C_1$–$C_2$-haloalkoxy, by reaction of 5-aminotriazole of the formula II

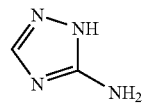

II with phenylmalonates of the formula III,

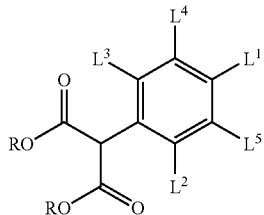

III to give dihydroxytriazolopyrimidines of the formula IV

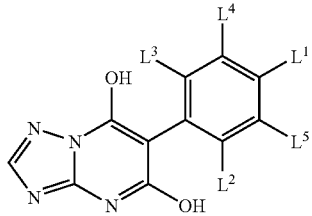

IV and halogenation to give the dihalogen compounds of the formula V,

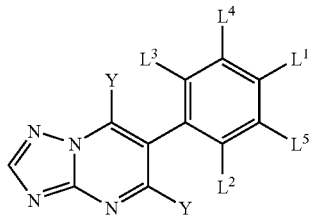

V in which Y is halogen, reaction with amines of the formula VI,

VI in which $R^1$ and $R^2$ have the meanings given in claim 2, to give 5-halo-7-aminotriazolopyrimidines of the formula I in which X is halogen, and, for the preparation of compounds of the formula I in which X represents cyano, $C_1$–$C_4$-alkoxy or $C_1$–$C_2$-haloalkoxy, reaction with compounds of the formula VII,

M-X'      VII which, according to the meaning of the group X' to be introduced, represents an inorganic cyanide, alkoxide or haloalkoxide and in which M is an ammonium, tetraalkylammonium, alkali metal or alkaline earth, metal cation.

7. A process for the preparation of the corn pounds of the formula I as claimed in claim 2 in which X is $C_1$–$C_4$-alkyl, by reaction of 5-aminotriazole of the formula II

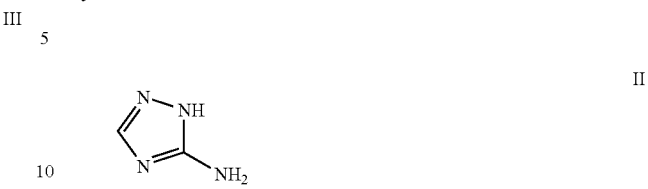

II with dicarbonyl compounds of the formula IIIa,

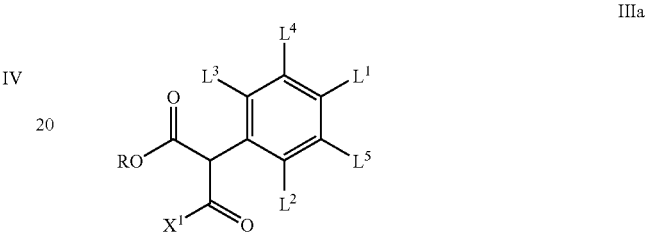

IIIa in which R and $X^1$ are $C_1$–$C_4$-alkyl, to give hydroxytriazolopyrimidines of the formula IVa

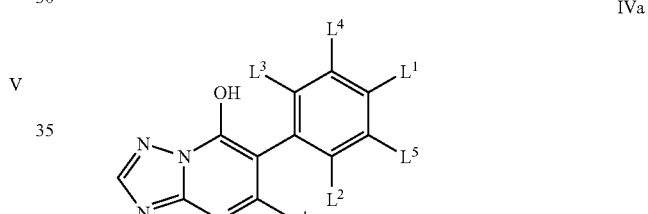

IVa halogenation to give compounds of the formula Va

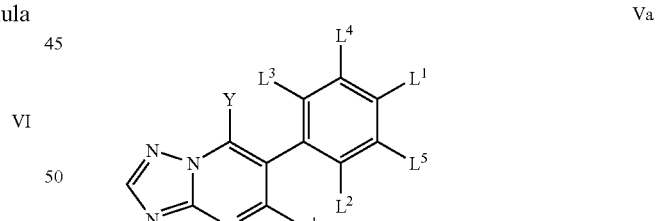

Va in which Y is halogen, and reaction with amines of the formula VI

VI in which $R^1$ and $R^2$ have the meanings given in claim 2, to give triazolopyrimidines of the formula I in which X is $C_1$–$C_4$alkyl.

8. A composition suitable for the control of harmful fungi, comprising a solid or liquid carrier and a compound of the formula I as claimed in claim 2.

9. A method for the control of harmful fungi, which comprises treating the fungi or the materials, plants, ground or seeds to be protected from fungal attack with an effective amount of a compound of the formula I as claimed in claim 2.

10. A compound of the formulae IIIa, IV, IVa, V and Va wherein
R is $C_1$–$C_4$-alkyl;
$X^1$ is $C_1$–$C_4$-alkyl;
Y is halogen;
$L^1$ is cyano, or C(=O)$A^2$, wherein
$A^2$ is $C_1$–$C_8$-alkoxy, $C_1$–$C_6$hydroxylkoxy, hydrogen, hydroxyl, $C_1$–$C_8$-alkyl, $C_1$–$C_8$-alkylamino or di($C_1$–$C_8$-alkyl)amino;
$L^2$, $L^3$ are hydrogen or halogen; and
$L^4$, $L^5$ are hydrogen, halogen or $C_1$–$C_4$alkyl.

* * * * *

UNITED STATES PATENT AND TRADEMARK OFFICE
CERTIFICATE OF CORRECTION

PATENT NO. : 7,148,227 B2
APPLICATION NO. : 10/508409
DATED : December 12, 2006
INVENTOR(S) : Blasco et al.

It is certified that error appears in the above-identified patent and that said Letters Patent is hereby corrected as shown below:

Claim 1, col. 28, indicated line 23: "S{O)$_n$A' or" should read --S{=O)$_n$A' or--

Claim 1, col. 28, indicated line 46: "subatituents" should read --substituents--

Claim 1, col. 28, indicated line 52: "$C_1C_6$-alkyl" should read --$C_1$-$C_6$-alkyl--

Claim 1, col. 28, indicated line 53: "$C_1$-$C_6$haloalkyl" should read --$C_1$-$C_6$-haloalkyl--

Claim 1, col. 28, indicated line 67: "alkcynyloxy" should read --alkynyloxy--

Claim 1, col. 29, indicated line 5: "dialkylamincarbonyl" should read --dialkylaminothiocarbonyl--

Claim 1, col. 29, indicated lines 10 – 11: "hetarocyclyloxy" should read --heterocyclyloxy--

Claim 2, col. 29, indicated line 37: "$C_1C_6$haloalkoxy" should read --$C_1$-$C_6$-haloalkoxy--

Claim 2, col. 29, indicated line 42: "$C_1$-$C_2$haloalkoxy" should read --$C_1$-$C_2$-haloalkoxy--

Claim 2, col. 29, indicated line 44: "$C_1$-$C_6$-haloalkyl" should read --$C_1$-$C_8$-haloalkyl--

Claim 2, col. 29, indicated line 45: "$C_3$-$C_6$halocycloalkyl" should read --$C_3$-$C_6$-halocycloalkyl--

Claim 2, col. 29, indicated line 46: "$C_2C_8$-haloalkenyl" should read --$C_2$-$C_8$-haloalkynyl--

Claim 2, col. 29, indicated line 47: "$C_2C_8$-haloalkynyl" should read --$C_2$-$C_8$-haloalkynyl--

Claim 2, col. 29, indicated line 65: "$C_1$-$C_6$alkyl" should read --$C_1$-$C_6$-alkyl--

Claim 2, col. 30, indicated line 1: "$C_1$-$C_6$alkylthio" should read --$C_1$-$C_6$-alkylthio--

Claim 2, col. 30, indicated line 2: "alkyl )amino" should read --alkyl)amino--

Claim 2, col. 30, indicated line 14: "aminocarbonyl, aminocarbonyl" should read --aminocarbonyl, aminothiocarbonyl--

UNITED STATES PATENT AND TRADEMARK OFFICE
CERTIFICATE OF CORRECTION

PATENT NO. : 7,148,227 B2
APPLICATION NO. : 10/508409
DATED : December 12, 2006
INVENTOR(S) : Blasco et al.

It is certified that error appears in the above-identified patent and that said Letters Patent is hereby corrected as shown below:

Claim 5: col. 30, indicated line 48: "$C_2$-$C_8$haloalkenyl" should read --$C_2$-$C_8$-haloalkenyl--

Claim 7, col. 32, indicated line 1: "corn pounds" should read --compounds--

Claim 7, col. 32, indicated line 67: "$C_1$-$C_4$alkyl" should read --$C_1$-$C_4$-alkyl--

Claim 10, col. 34, indicated line 42: "$C_1$-$C_6$hydroxylkoxy" should read --$C_1$-$C_6$-haloalkoxy--

Claim 10, col. 34, indicated line 47: "$C_1$-$C_4$alkyl" should read --$C_1$-$C_4$-alkyl--

Signed and Sealed this

First Day of May, 2007

JON W. DUDAS
*Director of the United States Patent and Trademark Office*